US012636390B2

(12) United States Patent
Licht

(10) Patent No.: US 12,636,390 B2
(45) Date of Patent: May 26, 2026

(54) SPRAY MECHANISM FOR SANITIZING AN AIRCRAFT

(71) Applicant: The Boeing Company, Chicago, IL (US)

(72) Inventor: Stephanie K. Licht, Everett, WA (US)

(73) Assignee: THE BOEING COMPANY, Arlington, VA (US)

( * ) Notice: Subject to any disclaimer, the term of this patent is extended or adjusted under 35 U.S.C. 154(b) by 925 days.

(21) Appl. No.: 17/352,167

(22) Filed: Jun. 18, 2021

(65) Prior Publication Data

US 2021/0393832 A1     Dec. 23, 2021

Related U.S. Application Data

(60) Provisional application No. 63/041,713, filed on Jun. 19, 2020.

(51) Int. Cl.
| | |
|---|---|
| *A61L 2/22* | (2006.01) |
| *A61L 2/26* | (2006.01) |
| *A61L 103/75* | (2026.01) |
| *B64D 13/06* | (2006.01) |
| *B64F 5/30* | (2017.01) |

(52) U.S. Cl.
CPC ...... *A61L 2/22* (2013.01); *A61L 2/26* (2013.01); *B64D 13/06* (2013.01); *B64F 5/30* (2017.01); *A61L 2103/75* (2026.01); *A61L 2202/15* (2013.01); *B64D 2013/0603* (2013.01)

(58) Field of Classification Search
CPC .......... A61L 2/22; A61L 2/26; A61L 2202/15; A61L 2202/25; A61L 2209/134; A61L 9/14; A61L 2202/14; A61L 2209/11; B64D 13/06; B64D 2013/0603; B64F 5/30

See application file for complete search history.

(56) References Cited

U.S. PATENT DOCUMENTS

| | | | | |
|---|---|---|---|---|
| 2012/0017630 A1* | 1/2012 | Okabe | ..................... | B05B 5/16 165/104.34 |
| 2014/0037496 A1* | 2/2014 | Pomeroy | ................... | A61L 2/24 422/111 |
| 2015/0190538 A1* | 7/2015 | Olvera | ..................... | A61L 2/24 250/455.11 |
| 2018/0193507 A1* | 7/2018 | Tapp | ......................... | E03C 1/10 |
| 2020/0198445 A1* | 6/2020 | Line | ......................... | A61L 9/20 |
| 2021/0338870 A1* | 11/2021 | Pess | ........................ | A61L 2/208 |

* cited by examiner

*Primary Examiner* — Brendan A Hensel
(74) *Attorney, Agent, or Firm* — MH2 Technology Law Group LLP

(57)     ABSTRACT

A sanitizing system includes a dispensing unit having a fluid storage and a compressed air generator. The fluid storage stores one or more disinfecting fluids or other sanitizing agents. The sanitizing system has an interconnect configured as an adapter that defines a conduit or passageway in an airflow path between a low pressure ground air supply and a connection port on an aircraft. The dispensing unit is configured to dispense the one or more disinfecting fluids or other sanitizing agents into the airflow path via the interconnect.

20 Claims, 7 Drawing Sheets

500

SPECIFICATION AND DESIGN — 502

MATERIAL PROCUREMENT — 504

COMPONENT AND SUBASSEMBLY MANUFACTURING — 506

SYSTEM INTEGRATION — 508

CERTIFICATION AND DELIVERY — 510

IN SERVICE — 512

MAINTENANCE AND SERVICE — 514

SPRAY MECHANISM FOR SANITIZING AN AIRCRAFT

CROSS-REFERENCE TO RELATED APPLICATION

This application claims the benefit of and priority to U.S. Provisional Application No. 63/041,713, entitled "Spray Mechanism for Sanitizing an Aircraft", filed June 19, 2020, which is incorporated by reference herein in its entirety.

BACKGROUND

Pathogens may be spread between humans, between animals, or between humans and animals in many different ways. As such, there is an increasing need for the disinfection or sterilization of public areas and public spaces, particularly enclosed areas and spaces. As one example, a single aircraft may fly to multiple destinations on the same day. These destinations may include, for example, different airports in the same state, in different states, or in different countries. Many passengers and crewmembers get on and off this single aircraft between flights. Further, the passengers and crewmembers onboard the aircraft during a single flight may be a diverse group coming from different backgrounds and environments. These conditions create the potential for the spread of pathogens onboard an aircraft.

To reduce the spread of pathogens in an aircraft, filtering of the air recirculated within the cabin is performed during flight. But, although the recirculated air in the aircraft cabin is filtered (e.g., high-efficiency particulate air (HEPA) filtering), the components of the environmental control system (ECS), such as the ducts, valves, etc. are not also cleaned and need to be cleaned. The wiping down of surfaces approach can result in missing some surfaces when cleaning, not completely cleaning the surfaces, etc. Thus, cleanliness and the overall sanitization of the cabin is affected. The manual wiping down approach is also time consuming, and as such, may also not be able to be satisfactorily performed in the limited time period when this cleaning is to occur (e.g., 20-30 minutes between deplaning and boarding of passenger at an airport gate), Thus, a need exists to efficiently and effectively disinfect or otherwise sanitize not only surfaces within aircraft cabin, but surfaces that deliver airflow to the aircraft cabin.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one example, a sanitizing system comprises a dispensing unit having a fluid storage and a compressed air generator. The fluid storage stores one or more disinfecting fluids or other sanitizing agents. The sanitizing system further comprises an interconnect configured as an adapter that defines a conduit or passageway in an airflow path between a low pressure ground air supply and a connection port on an aircraft. The dispensing unit is configured to dispense the one or more disinfecting fluids or other sanitizing agents into the airflow path via the interconnect.

In another example, a method for sanitizing an aircraft includes configuring a sanitizing system to receive an activation signal. The sanitizing system includes a dispensing unit having a fluid storage and a compressed air generator, wherein the fluid storage stores one or more disinfecting fluids or other sanitizing agents. The sanitizing system further includes an interconnect configured as an adapter that defines a conduit or passageway in an airflow path between a low pressure ground air supply and a connection port on the aircraft, wherein the dispensing unit is configured to dispense the one or more disinfecting fluids or other sanitizing agents into the airflow path via the interconnect. The method further includes dispensing the one or more disinfecting fluids or other sanitizing agents into the airflow path via the interconnect in response to receiving the activation signal.

Many of the attendant features will be more readily appreciated as the same becomes better understood by reference to the following detailed description considered in connection with the accompanying drawings.

DETAILED DESCRIPTION

Figure 1:
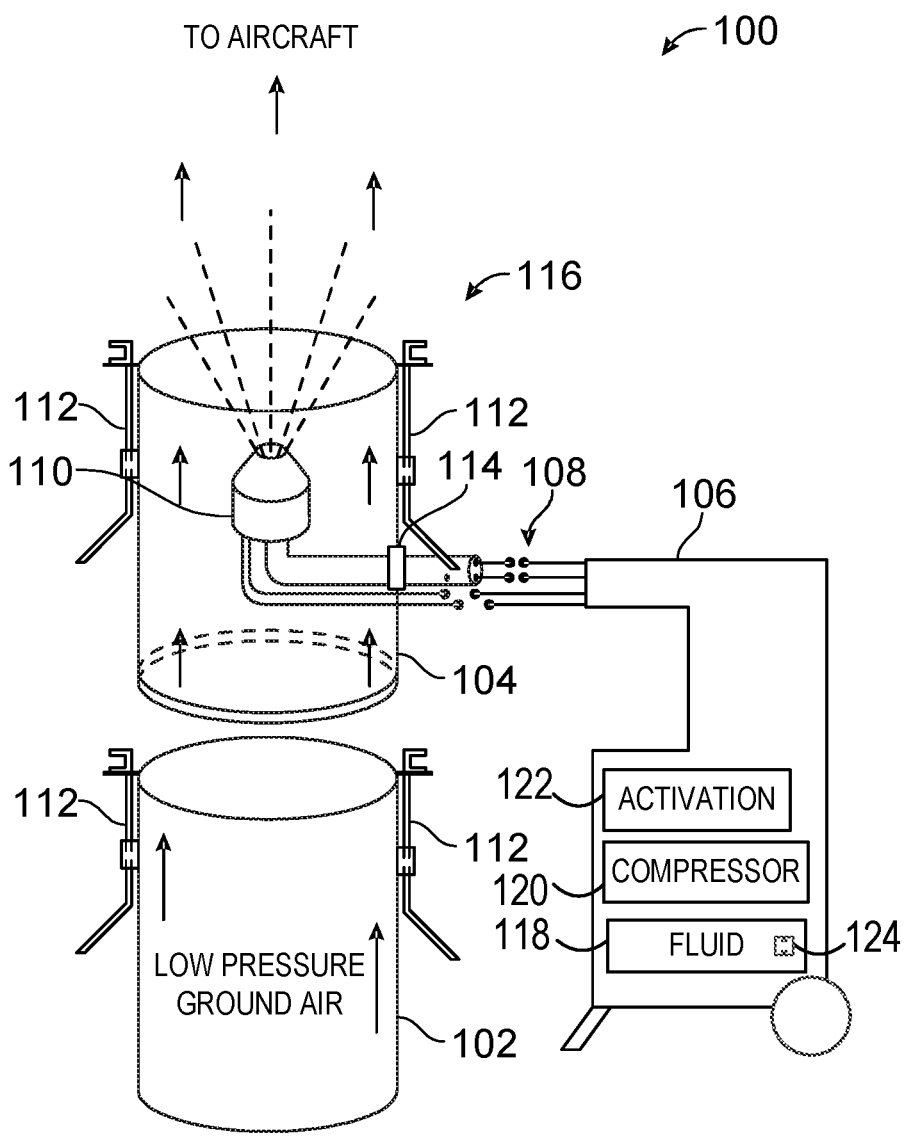
FIG. 1 is a diagram of a sanitizing system according to an implementation.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" or "one implementation" are not intended to be interpreted as excluding the existence of additional embodiments or implementations that also incorporate the recited features. Moreover, unless explicitly stated to the contrary, embodiments "comprising" or "having" an element or a plurality of elements having a particular property can include additional elements not having that property.

Implementations of the systems, methods, and devices described herein enable sanitizing or disinfecting of surfaces within an aircraft, including surfaces of the air delivery components (e.g., ECS components) within the aircraft that deliver airflow to the cabin. In one implementation, the aircraft ECS is used as the disinfectant "applicator", which reduces the time that would otherwise be needed for spray and wipe type cleaning. In one example, a disinfecting unit (also referred to as a cleaning unit) is configured to couple inline between a low pressure ground connection preconditioned air unit (PCA) and a ground cart air supply hose. The disinfecting unit is configured in some examples as a dispensing unit that houses a mechanism having an adapter for fogging, electrostatic spraying, ion generation, or introduction of gaseous cleaner/disinfectants into the cabin air supply ducting via a mix manifold.

With the examples described herein, disinfectant can be rapidly applied to the entire airplane interior, including surfaces that otherwise cannot be easily cleaned by a wiping down approach (e.g., allows surfaces that would otherwise not be treated outside maintenance checks to be treated). The rapid application of disinfectant allows the aircraft to be effectively and easily cleaned/sanitized with short turn-around times via no-touch methods. That is, the time it takes for an aircraft to be disinfected is reduced, and in some environments, the number of personnel to perform the cleaning is reduced. Thus, the time, cost, and potentially reduced quality of manual application of disinfectants is reduced.

One or more herein described examples solve aircraft sanitizing issues by providing an arrangement having a blower removably coupled to a mixing chamber. The blower is positioned below the mixing chamber and is configured to drive air to and through the mixing chamber. The mixing chamber has a nozzle therein configured to introduce a cleaning agent into the airflow (e.g., oriented to dispense the agent in the direction of the flow) through a discharge port of the mixing chamber that leads to a manifold of the ECS of an aircraft. The nozzle is connected to a compressor cart that stores the agent and delivers the agent to the nozzle via a line connected therebetween.

Figure 2:
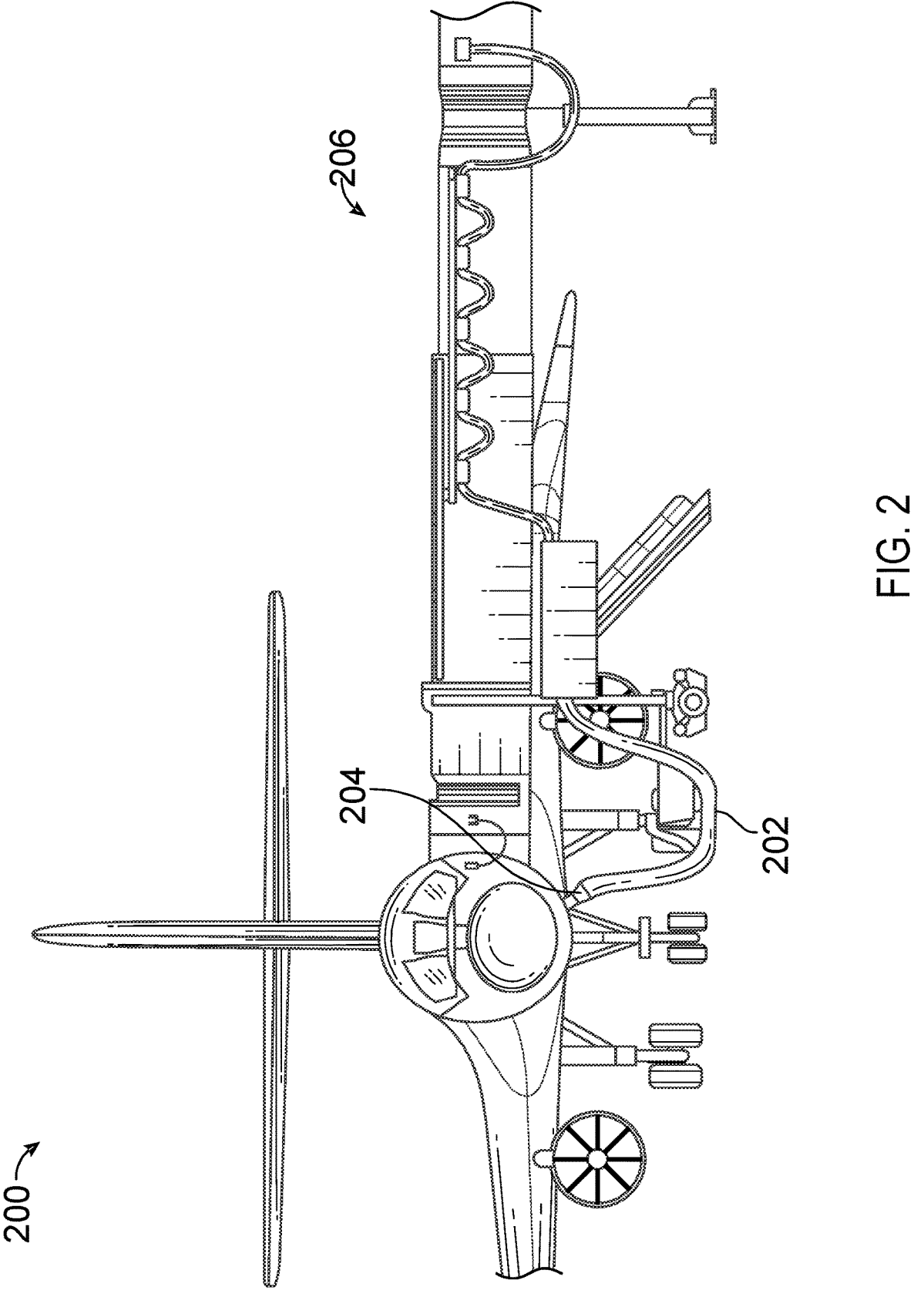
FIG. 2 is a diagram illustrating an aircraft environment in which the sanitizing system of FIG. 1 can be implemented.

With particular reference to FIGS. 1 and 2, a sanitizing system 100 (e.g., configured as a ground cart that is movable) is illustrated and configured to couple to an air supply 102 (e.g., a low pressure ground air supply) connected to an aircraft 200 when on the ground (e.g. parked at an airport gate), which is illustrated as being coupled in-line with a hose 202 of the air supply 102. In the illustrated configuration, an interconnect 104, which can be any type of coupling mechanism or adapter (e.g., an in-line hose or tube) that provides coupling between the air supply 102 and the connection interface or port 204 on the aircraft 200, allows for fluid connection of a dispensing unit 106 to the air supply 102. With this fluid connection, the dispensing unit 106 is operable to dispense, for example, a disinfecting fluid within the air flow (represented by the arrows) being supplied to the aircraft 200 (e.g., an external agent is injected into the air flow).

With particular reference to FIG. 1, the dispensing unit 106 includes one or more supply lines 108 connected between the dispensing unit 106 and a dispensing end 110 within the interconnect 104. In the illustrated example, the dispensing end 110 is a nozzle (e.g., a nozzle of an electrostatic sprayer or electrostatic spray gun) configured to dispense (e.g., spray) disinfecting fluid or other sanitizing agents into the inner portion of the interconnect 104 that defines a conduit or passageway in the airflow path between the air supply 102 and the port 204 (e.g., positioned within an airflow path into the aircraft 200). In this way, when the disinfecting fluid or other sanitizing agents are dispensed into the interconnect 104, the airflow therethrough carries the disinfecting fluid or other sanitizing agents into the aircraft 200, such as into an ECS 302 (in FIG. 3). As a result, the disinfecting fluid or other sanitizing agents are spread throughout the aircraft 200, including through the various components (e.g., ducts) of the ECS 302 and into the cabin of the aircraft 200. That is, in some examples, the disinfecting fluid or other sanitizing agents is dispensed and provided directly into the ECS 302 and then into the cabin of the aircraft 200.

The amount of disinfecting fluid or other sanitizing agents dispensed by the dispensing unit is selectively controllable, such as by adjusting a flow rate or flow time of the disinfecting fluid or other sanitizing agents (or air flow) from the dispensing unit 106 and through the one or more supply lines 108 to the dispensing end 110. In some examples, the dispensing end 110 can be changed, such as to switch between different types of nozzles or dispensing ports as desired or needed (e.g., based on the type of sanitizing agent, the desired flow rate, etc.). In one example, the one or more supply lines 108 include one or more fluid supply lines and one or more compressed air supply lines that allow the disinfecting fluid or other sanitizing agents and compressed air, respectively, to be provided to the dispensing end 110.

In the illustrated example, the dispensing unit 106 includes (i) a fluid container 118 (or storage vessel) that holds the disinfecting fluid or other sanitizing agents to supply the disinfecting fluid or other sanitizing agents through the one or more supply lines 108 and that can be replenished as needed, and (ii) a compressed air supply unit, illustrated as an air compressor 120 configured to supply compressed air through the one or more compressed air supply lines. Other supply lines are contemplated, for example, electrical supply lines that provide electrical power as needed. It should be noted that the one or more supply lines 108 in some examples are dedicated supply lines to provide (i) the disinfecting fluid or other sanitizing agents or (ii) the compressed air. In other examples, the one or more supply lines 108 are configured to selectively provide (i) the disinfecting fluid or other sanitizing agents and (ii) the compressed air. That is, in some examples, each of the one or more supply lines 108 is configured to deliver different types of fluids therethrough.

The dispensing components, including the one or more supply lines 108 to the dispensing end 110 can be integrated with or removably coupled to the interconnect 104. For example, the one or more supply lines 108, in one example, extend through a wall of the interconnect 104 to the dispensing end 110. The passageway or opening through which the one or more supply lines 108 pass is sealed, such as with a rubber grommet 114 or other suitable fluid sealing member or material (e.g., epoxy) to prevent air and fluid from leaking out of the interconnect 104 when dispensing the disinfecting fluid or other sanitizing agents. It should be appreciated that the configuration of the dispensing components can be varied as desired or needed. For example, the size, shape, position, orientation, etc. of the dispensing components, such as the position and orientation of the dispensing end 110 within the interconnect 104 can be changed based on the particular application, configuration of the air supply 102, the configuration of one or more hoses, etc.

In operation, the interconnect 104 is coupled between the air supply 102 and the aircraft 200, particularly the connection port 204 of the aircraft 200 using complementary coupling members 112 (illustrated as snap-fit types of connectors having handles to facilitate movement and coupling operation). It should be appreciated that the coupling members 112 can be any type of coupling mechanism and can be located on different ones of the air supply 102, interconnect 104 and connection port 204. In one example, the interconnect 104 includes coupling members 112 that are connection or engagement members that are configured to connect to the air supply 102 on one end and the connection port 204 on the other end. In this way, an easily connectable inline arrangement is defined that allows for quick setup to thereafter supply the disinfecting fluid or other sanitizing agents to the aircraft 200, such as when the aircraft is parked at an air bridge 206. For example, with this quick connect arrangement, a spray 116 of the disinfecting fluid or other sanitizing agents can be generated within the air supply path to the ECS 302 of the aircraft 200 in a short amount of time between passengers deplaning the aircraft 200 and then passengers boarding the aircraft 200. In one example, the herein described configurations allow for the disinfecting fluid or other sanitizing agents to be easily and quickly dispensed into and throughout the aircraft 200 without manual wiping of the many surfaces within the aircraft 200. However, it should be appreciated that in some examples, manual wiping of one or more of the surfaces within the aircraft 200, such as within the cabin of the aircraft 200, can be performed in combination with the spraying of the disinfecting fluid or other sanitizing agents by the sanitizing system 100. As illustrated, interconnect 104 has a cylindrical shape with an inlet side of interconnect 104 being removably mateable with an outlet of the ground air supply preconditioned air unit (PCA) 102 via a first set of coupling members 112 associated with the preconditioned air unit (PCA) 102. Similarly, an outlet side of interconnect 104, positioned directly opposite to the inlet side of interconnect 104, is removably mateable with the connection port 204 on the aircraft via a second set of coupling members 112 associated with the interconnect, where a dispensing end 110 of the dispensing unit 106 is located within the interconnect 104.

The interconnect 104 is also configured to have a shape and size that is complementary with the air supply 102 and connection port 204. In one example, the interconnect 104 is tubular shaped and sized to couple and fluidly seal with the air supply 102 on one end and the connection port 204 on another end. In another example, the interconnect 104 is tubular shaped and sized to couple and fluidly seal with a hose of the air supply 102 on one or both ends (e.g., configured as an inline hose adapter). It should be appreciated that the interconnect 104 can be formed from different materials that are rigid, semi-rigid, or flexible. For example, the interconnect 104 in various examples is a rigid tube or conduit, and in other examples, a flexible tube or conduit.

The dispensing unit 106 in some examples includes an activation system 122 that controls activation and deactivation of the disinfection process, including the amount and time period during which the disinfecting fluid or other sanitizing agents is dispensed (e.g., controls operation of the compressor 120 and fluid flow from the fluid container 118. For example, a determination is made as to whether a set of criteria for activation of the sanitizing system 100 that dispenses the disinfecting fluid or other sanitizing agents inside the aircraft 200, has been met (e.g., no passengers in the cabin of the aircraft 200). In response to a determination that the set of criteria has been met, the sanitizing system 100 is activated (e.g., fluid and air flow started) to perform the sanitizing or disinfection process inside the aircraft 200 using the disinfecting fluid or other sanitizing agents. An activation signal generated by the activation system 122 can be used to activate the dispensing unit 106, which can be a manually initiated signal (e.g., push button from a user) or automatically initiated signal (e.g., automatic detection of no passengers in the cabin of the aircraft 200).

The disinfecting fluid or other sanitizing agents can be supplied to the air path to be conveyed to the ECS 302 using any suitable fluid conduit, such as a pipe, tube, or the like that is configured to receive one or more fluids. In one example, the dispensing unit 106 includes one or more sub-systems that are coupled through one or more wired or wireless connections to control operation of the various components, such as one or more valves 124 that control the amount and time period that the disinfecting fluid or other sanitizing agents are dispensed from the dispensing unit 106.

Figure 3:
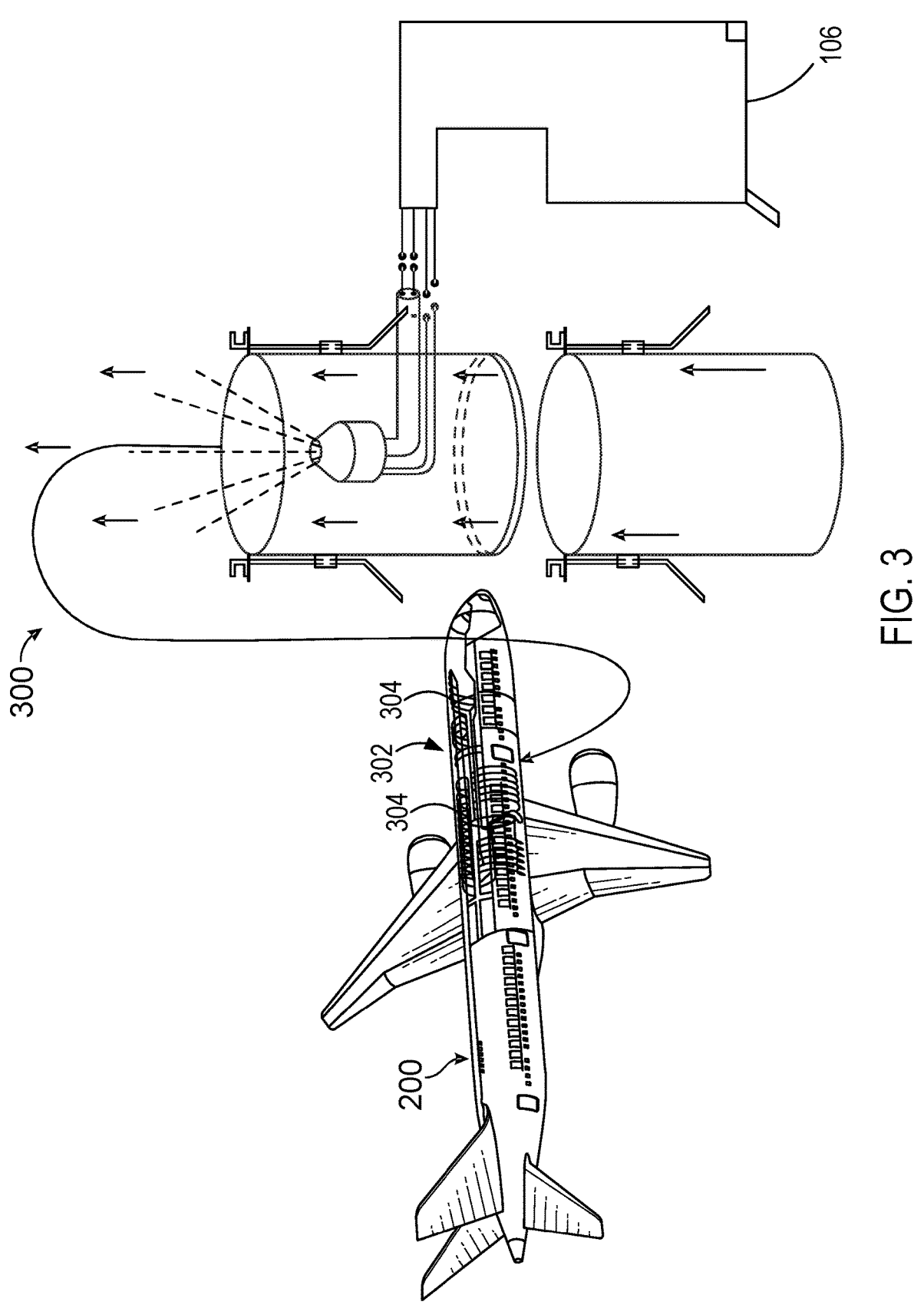
FIG. 3 is a diagram illustrating a sanitizing flow according to an implementation.

Thus, the sanitizing system 100 in various examples operates to dispense disinfecting fluid or other sanitizing agents to perform a disinfection or sanitizing process 300 (as shown in FIG. 3) inside the aircraft 200, including components that are not otherwise easily accessible (e.g., ducts 304 within the ECS 302). In one example, the sanitizing system 100 dispenses the disinfecting fluid or other sanitizing agents to a plurality of surfaces withing the aircraft 200, such as surfaces that may need to be disinfected due to the potential for contact (which may be physical contact or air contact) with at least one of a person, animal, or object carrying any number of pathogens. In one example, the amount of disinfecting fluid or other sanitizing agents flowing to the ECS 302 is controllable as described in more detail herein.

It should be appreciated that although the various examples have been described in connection with dispensing disinfecting fluid or other sanitizing agents into the aircraft 200, one or more examples can be used to dispense different type of fluids into the aircraft 200, or into other vehicles (e.g., ground vehicle or water vehicle) or non-vehicles (e.g., buildings), which can be non-sanitizing (e.g., an odor removing spray). Additionally, in an aerospace application, one or more examples can be implemented in connection with any type of aircraft. In some examples, the systems described herein are configured to dispense disinfecting fluid or other sanitizing agents into any confined space.

It should also be appreciated that although the examples described herein use disinfecting fluids or other sanitizing agents, different types of disinfectant sprays, aerosols, or other types of cleaning fluids can be used to disinfect surfaces. In some examples, other cleaning arrangements can be used, such as an electrostatic sprayer (e.g., an electrostatic spray gun), a fogger, or an ion generator, among others. In some example, the disinfecting fluid or other sanitizing agents are selected to be compatible with the surfaces of the aircraft 200, namely that do not cause material degradation of the of the aircraft parts (e.g., compatible with interior components and system components of the aircraft 200, such as the ECS 302, avionics, flight deck, etc.).

In various examples, the aircraft ECS 302 is thereby treated by a spray mechanism via the low pressure ground connection. The dispensing unit 106 is attached to the low pressure ground connection on one side, and the PCA/ground cart air supply hose on the other. Within the unit dispensing unit 106 are one or more mechanisms that allow an adapter for fogging, electrostatic spraying, or introduction of gaseous cleaner/disinfectants to enter the air supply ducting (and then cabin of the aircraft 200) via a mixing manifold. With the herein described examples, a problem that is solved is the need to clean the aircraft 200 with short turnaround times via no-touch methods. In one more examples, the time to disinfect the aircraft 200 and/or the number of personnel to perform the disinfecting is reduced. In addition, various examples allow surfaces that would otherwise not be treated outside maintenance checks to be treated.

Figure 4:
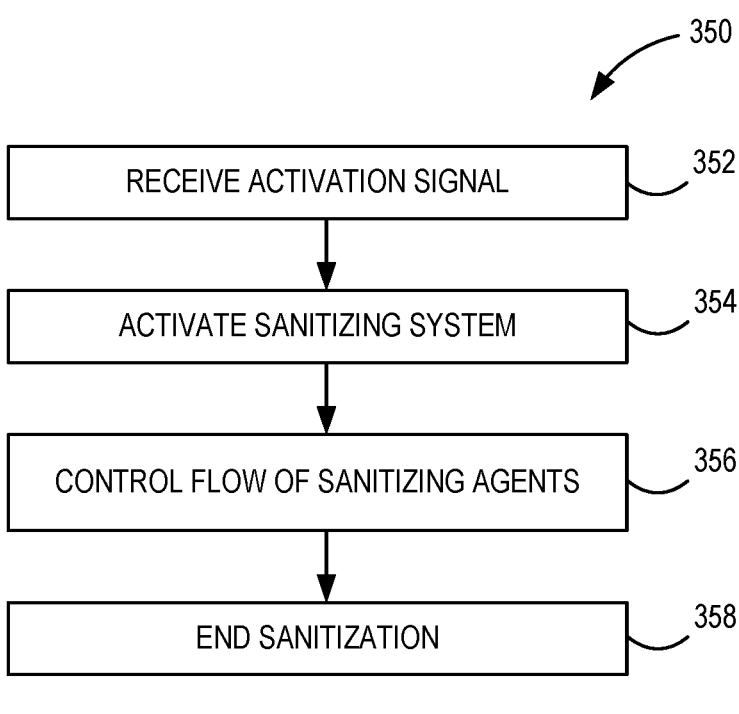
FIG. 4 is a block diagram of a disinfecting process according to an implementation.

For example, a disinfecting process 350 as illustrated in FIG. 4 is performed. In one example, a sanitizing system (e.g., the sanitizing system 100) is configured to perform the disinfecting process 350. The disinfecting process 350 includes receiving an activation signal at 352. As described in more detail herein, the activation signal can be initiated in response to an automatic generation of an input (e.g., sensor detecting that the aircraft is not occupied by passengers or crew) or a manual generation of an input (e.g., user depressing an activation button). A sanitizing system (e.g., the sanitizing system 100) is the activated at 354. For example, the flow of disinfecting fluid or other sanitizing agents is initiated, which is dispensed into the air flow into the aircraft, such as using a connect, interface, or port to access one or more air systems within the aircraft (e.g., to the ECS 302).

The flow of the disinfecting fluid or other sanitizing agents is controlled at 356. For example, the amount of disinfecting fluid or other sanitizing agents dispensed (e.g., flow rate of the disinfecting fluid or other sanitizing agents, total amount of disinfecting fluid or other sanitizing agents dispensed, etc.) can be varied or changed, such as based on disinfecting requirements, the size of the aircraft, etc. The control can be performed using one or signals and based on feedback in some examples. For example, user feedback or sensor feedback that indicates a level of sanitation can be used to adjust one or more settings for dispensing the disinfecting fluid or other sanitizing agents. The sanitization operation or processed is ended at 358, such as based on a defined time period, a defined amount of dispensed disinfecting fluid or other sanitizing agents, etc.

Thus, in various examples, cleaners are introduced into the supply air ducting, such as through the mixing manifold via the low pressure ground connection. As a result, manual spraying and wipe type cleaning is not needed in various examples. As such, various examples provide infection control and prevention, including methods of cleaning the ECS 302 of the aircraft 200. In one or more examples, a modular system is thereby provided for cleaning the ECS 302.

Exemplary Operating Environment

Figure 5:
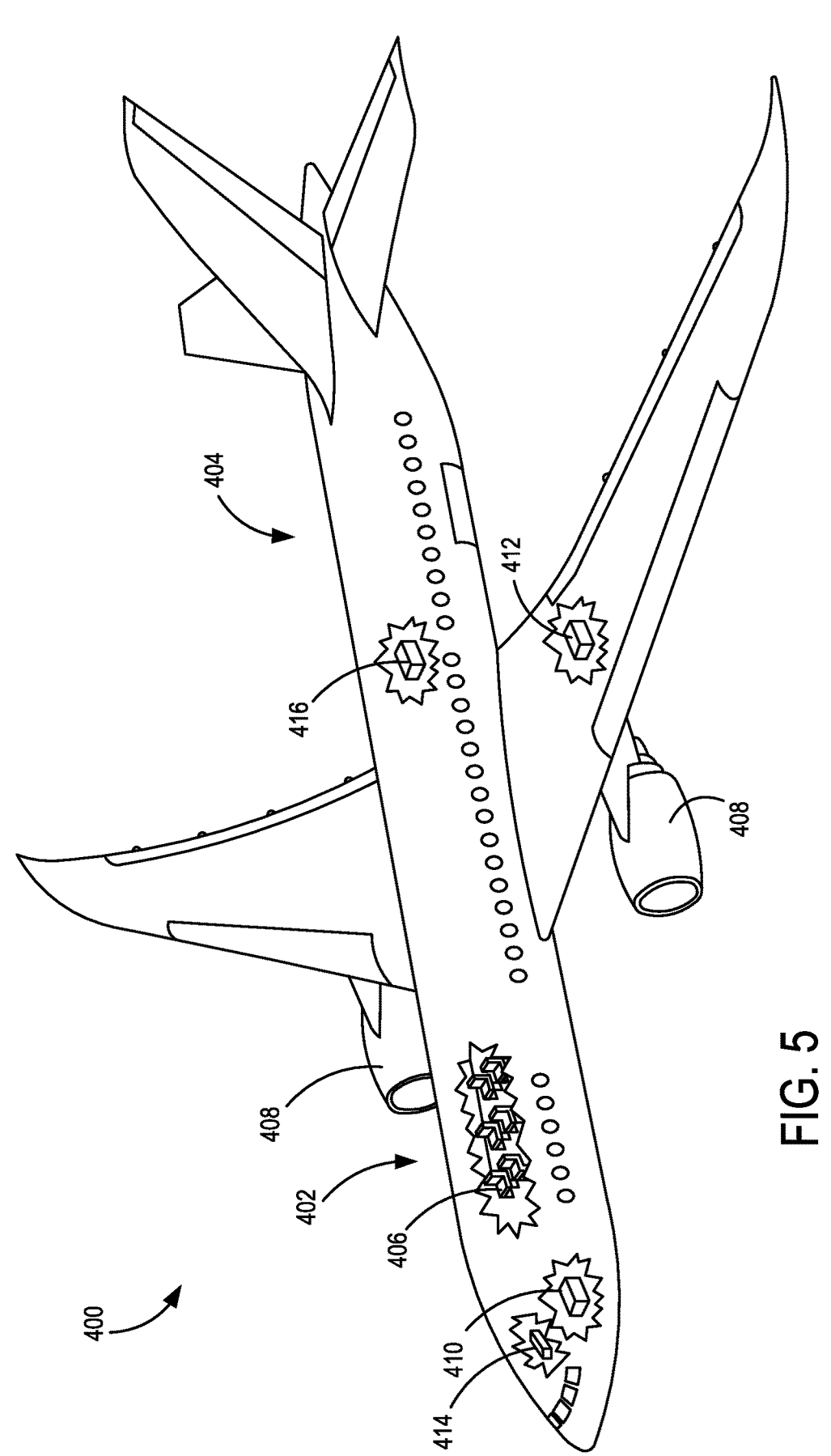
FIG. 5 is a schematic perspective view of an aircraft.

Referring now to FIG. 5, implementations are operable with an and can be described in the context of an aircraft 400 (which can be embodied in part or whole as the aircraft 200) having an airframe 402 with a plurality of high-level systems 404 and an interior 406. Examples of high-level systems 404 include one or more of a propulsion system 408, an electrical system 410, a hydraulic fluid system 412, a control system 414, and an environmental system 416. Any number of other systems can be included. Although an aerospace example is shown, the principles can be applied to other industries, such as, but not limited to, the automotive industry, the marine industry, etc.

Figure 6:
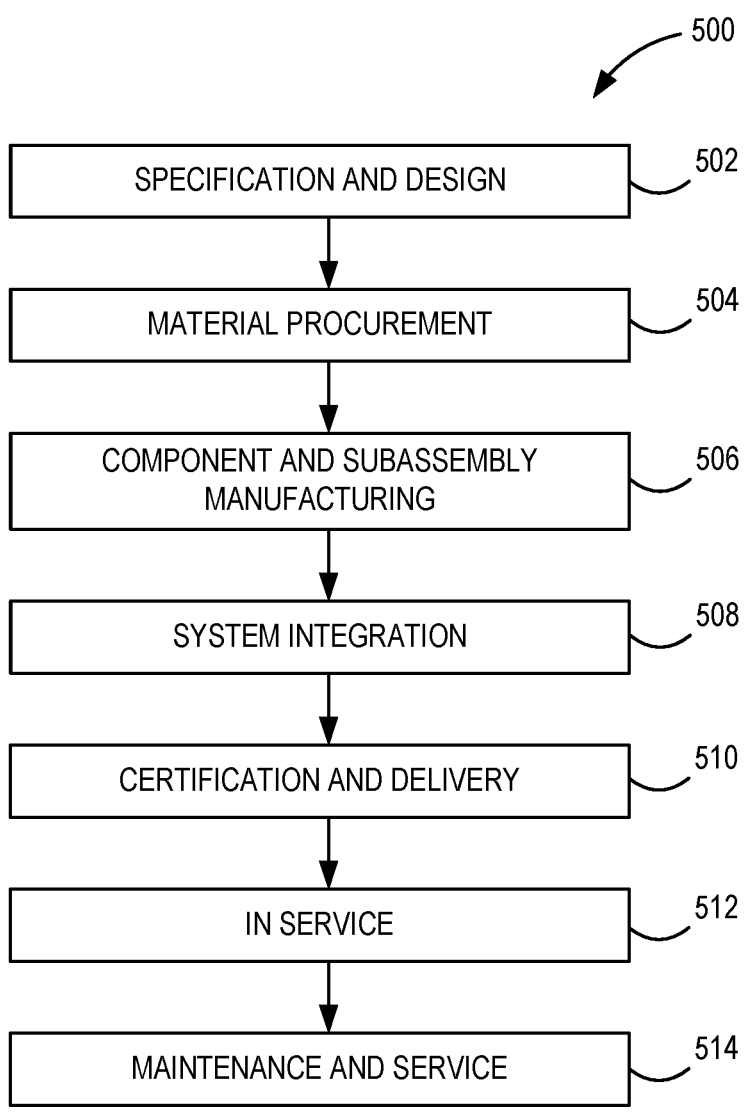
FIG. 6 is a block diagram of an aircraft production and service methodology.

Implementations can be described in the context of an aircraft manufacturing and service method 500 as shown in FIG. 6. During pre-production, illustrative method 500 includes specification and design 502 of an aircraft (e.g., aircraft 400 shown in FIG. 5) and material procurement 504. During production, component and subassembly manufacturing 506 and system integration 508 of the aircraft take place. Thereafter, the aircraft goes through certification and delivery 510 to be placed in service 512. While in service by a customer, the aircraft is scheduled for routine maintenance and service 514 (which in some implementations also includes modification, reconfiguration, refurbishment, and so on).

Each of the processes of the illustrative method 500 can be performed or carried out by a system integrator, a third party, and/or an operator (e.g., a customer). For the purposes of this description, a system integrator includes, without limitation, any number of aircraft manufacturers and major-system subcontractors; a third party includes, without limitation, any number of vendors, subcontractors, and suppliers; and an operator includes, without limitation, an airline, leasing company, military entity, service organization, and so on.

It should be noted that any number of other systems can be included with the system described herein. Also, although an aerospace example is shown, the principles can be applied to other industries, such as, but not limited to, the automotive industry, the marine industry, etc.

Systems and methods shown or described herein are, in some implementations, employed during any one or more of the stages of the manufacturing and service method 500. For example, components or subassemblies corresponding to component and subassembly manufacturing 506 are, in some implementations, fabricated or manufactured in a manner similar to components or subassemblies produced while the aircraft is in service. Also, one or more aspects of the system, method, or combination thereof are utilized, in some implementations, during the production states of subassembly manufacturing 506 and system integration 508, for example, by substantially expediting assembly of or reducing the cost of the aircraft. Similarly, in some implementations, one or more aspects of the apparatus or method realizations, or a combination thereof, are utilized, for example and without limitation, while the aircraft is in service, e.g., maintenance and service 514.

Figure 7:
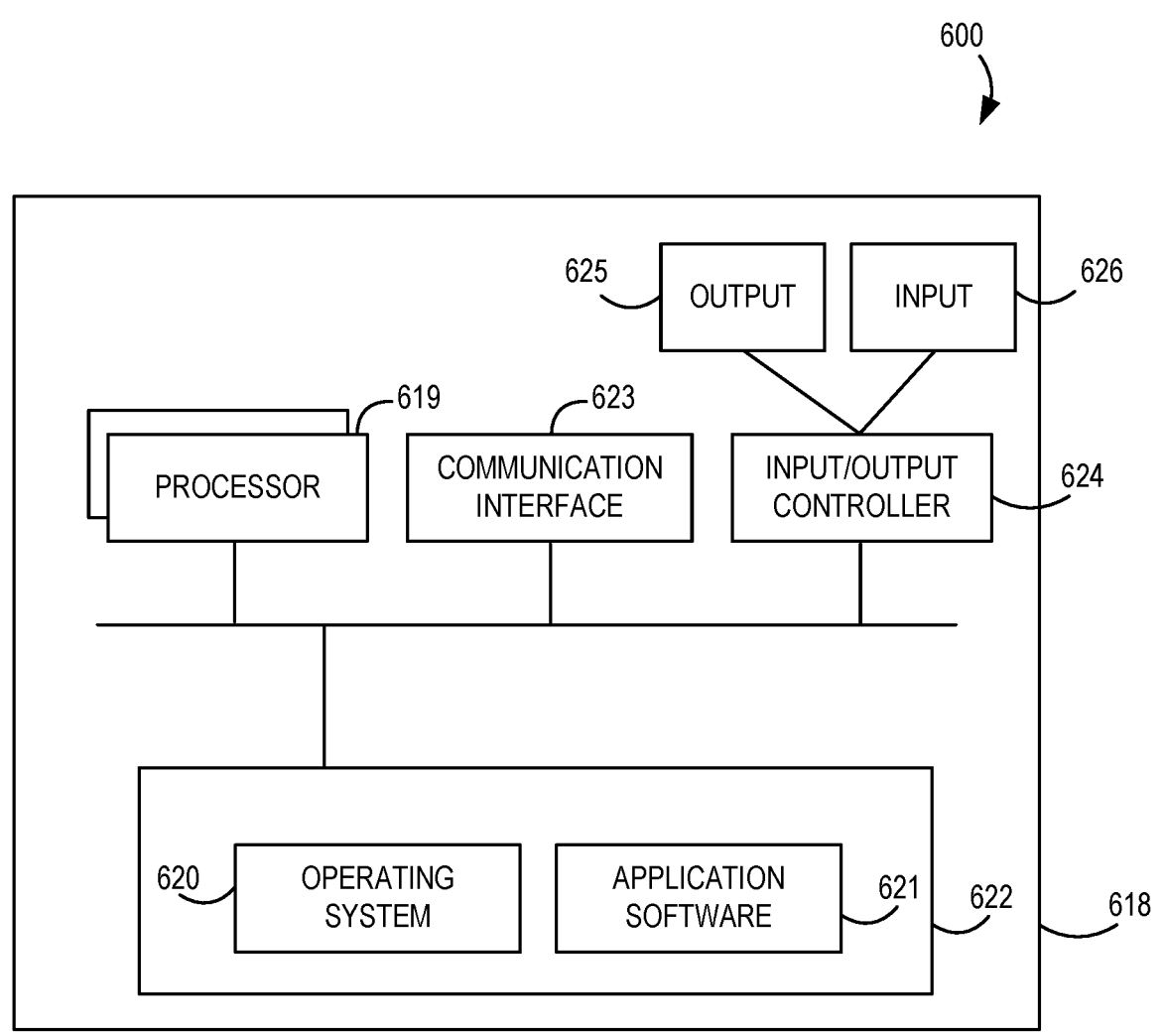
FIG. 7 illustrates an electronic device according to an implementation as a functional block diagram.

One or more examples are operable with an electronic device (i.e., a computing apparatus) according to an implementation as a functional block diagram 600 in FIG. 7. In an implementation, components of a computing apparatus 618 are implemented as a part of an electronic device according to one or more implementations described in this specification (e.g., control components of the dispensing unit 106). The computing apparatus 618 comprises one or more processors 619, for example microprocessors, controllers, and/or any other suitable type of processors for processing computer executable instructions to control the operation of the electronic device. In some implementations, platform software comprising an operating system 620 and/or any other suitable platform software is provided on the apparatus 618 to enable application software 621 to be executed on the device.

Computer executable instructions are provided using any computer-readable media that are accessible by the computing apparatus 618. Computer-readable media include, for example and without limitation, computer storage media such as a memory 622 and communications media. Computer storage media, such as a memory 622, include volatile and non-volatile, removable and non-removable media implemented in any method or technology for storage of information such as computer readable instructions, data structures, program modules or the like. Computer storage media include, but are not limited to, RAM, ROM, EPROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing apparatus. In contrast, communication media embody computer readable instructions, data structures, program modules, and/or the like in a modulated data signal, such as a carrier wave and/or other transport mechanism. As defined herein, computer storage media do not include communication media. Therefore, a computer storage medium should not be interpreted to be a propagating signal per se. Propagated signals per se are not examples of computer storage media. Although the computer storage medium (the memory 622) is shown within the computing apparatus 618, it will be appreciated by a person skilled in the art, that in some implementations the storage is distributed or located remotely and accessed via a network or other communication link (e.g. using a communication interface 623).

In some implementations, the computing apparatus 618 comprises an input/output controller 624 configured to output information to one or more output devices 625, for example a display and/or a speaker, which is separate from or integral to the electronic device. The input/output controller 624 is also configured, in some implementations, to receive and process an input from one or more input devices 626, for example, a keyboard, a microphone, and/or a touchpad. In one implementation, the output device 625 also acts as the input device. An example of such a device is a touch sensitive display. In some implementations, the input/output controller 624 also outputs data to devices other than the output device, e.g. a locally connected printing device. In some implementations, a user 627 provides input to the input device(s) 626 and/or receives output from the output device (s) 625.

In some implementations, the functionality described herein is performed, at least in part, by one or more hardware logic components. According to an implementation, the computing apparatus 618 is configured by the program code when executed by the processor 619 to execute the implementations of the operations and functionality described. Alternatively, or in addition, the functionality described herein is performed, at least in part, by one or more hardware logic components. For example, and without limitation, illustrative types of hardware logic components include Field-programmable Gate Arrays (FPGAs), Application-specific Integrated Circuits (ASICs), Program-specific Standard Products (ASSPs), System-on-a-chip systems (SOCs), Complex Programmable Logic Devices (CPLDs), Graphics Processing Units (GPUs), and/or the like.

Although some of the present embodiments are described and illustrated as being implemented in a server, controller, cloud service, smartphone, mobile phone, personal computer, and/or tablet computer, these are only examples of a device and not a limitation. As those skilled in the art will appreciate, the present implementations are suitable for application in a wide variety of different types of devices, such as portable and mobile devices, for example, in laptop computers, tablet computers, etc.

At least a portion of the functionality of the various elements in the figures may be performed by other elements in the figures, or an entity (e.g., processor, web service, server, application program, computing device, etc.) not shown in the figures.

Although described in connection with an exemplary computing system environment, one or more examples are capable of implementation with numerous other general purpose or special purpose computing system environments, configurations, and/or devices.

Examples of well-known computing systems, environments, and/or configurations that may be suitable for use with aspects described herein include, but are not limited to, mobile computing devices, personal computers, server computers, hand-held or laptop devices, multiprocessor systems, microprocessor-based systems, set top boxes, programmable consumer electronics, mobile telephones, mobile computing and/or communication devices, network PCs, minicomputers, mainframe computers, distributed computing environments that include any of the above systems and/or devices, and/or the like. Such systems and/or devices may accept input from the user in any way, including from input devices such as a keyboard or pointing device, via gesture input, proximity input (for example by hovering), and/or via voice input.

Implementations may be described in the general context of computer-executable instructions, such as program modules, executed by one or more computers or other devices in software, firmware, hardware, or a combination thereof. The computer-executable instructions may be organized into one or more computer-executable components or modules. Generally, program modules include, but are not limited to, routines, programs, objects, components, and data structures that perform particular tasks or implement particular abstract data types. Aspects and implementations may be implemented with any number and organization of such components or modules. For example, aspects and implementations described herein are not limited to the specific computer-executable instructions or the specific components or modules illustrated in the figures and described herein. Other may include different computer-executable instructions and/or components having more or less functionality than illustrated and described herein.

In examples involving a general-purpose computer, aspects and implementations transform the general-purpose computer into a special-purpose computing device when configured to execute the instructions described herein.

The examples and implementations illustrated and/or described herein as well as examples and implementations not specifically described herein but within the scope of aspects and implementations various examples constitute exemplary means for sanitization of spaces.

Any range or device value given herein may be extended or altered without losing the effect sought, as will be apparent to the skilled person.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It will be understood that the benefits and advantages described above may relate to one implementation or may relate to several implementations. The implementations are not limited to those that solve any or all of the stated problems or those that have any or all of the stated benefits and advantages. It will further be understood that reference to 'an' item refers to one or more of those items.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

The term "comprising" is used in this specification to mean including the feature(s) or act(s) followed thereafter, without excluding the presence of one or more additional features or acts. The terms "comprising," "including," and "having" are intended to be inclusive and mean that there can be additional elements other than the listed elements. In other words, the use of "including," "comprising," "having," "containing," "involving," and variations thereof, is meant to encompass the items listed thereafter and additional items. Further, references to "one implementation" are not intended to be interpreted as excluding the existence of additional implementations that also incorporate the recited features. The term "exemplary" is intended to mean "an example of".

When introducing elements of aspects and implementations or the examples thereof, the articles "a," "an," "the," and "said" are intended to mean that there are one or more of the elements. In other words, the indefinite articles "a", "an", "the", and "said" as used in the specification and in the claims, unless clearly indicated to the contrary, should be understood to mean "at least one."

The phrase "one or more of the following: A, B, and C" means "at least one of A and/or at least one of B and/or at least one of C." The phrase "and/or", as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one implementation, to A only (optionally including elements other than B); in another implementation, to B only (optionally including elements other than A); in yet another implementation, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of" or, when used in the claims, "consisting of" will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one implementation, to at least one, optionally including more than one, A, with no B present (and optionally including elements other than B); in another implementation, to at least one, optionally including more than one, B, with no A present (and optionally including elements other than A); in yet another implementation, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

Having described aspects of the various examples in detail, it will be apparent that modifications and variations are possible without departing from the scope of aspects as defined in the appended claims. As various changes could be made in the above constructions, products, and methods without departing from the scope of aspects describe herein, it is intended that all matter contained in the above description and shown in the accompanying drawings shall be interpreted as illustrative and not in a limiting sense.

It is to be understood that the above description is intended to be illustrative, and not restrictive. For example, the above-described implementations (and/or aspects thereof) can be used in combination with each other. In addition, many modifications can be made to adapt a particular situation or material to the teachings of the various implementations described herein without departing from their scope. While the dimensions and types of materials described herein are intended to define the parameters of the various implementations described herein, the implementations are by no means limiting and are example implementations. Many other implementations will be apparent to those of ordinary skill in the art upon reviewing the above description. The scope of the various implementations described herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 122(f), unless and until such claim limitations expressly use the phrase "means for" followed by a statement of function void of further structure.

This written description uses examples to disclose the various implementations, including the best mode, and also to enable any person of ordinary skill in the art to practice the various implementations, including making and using any devices or systems and performing any incorporated methods. The patentable scope of the various implementations is defined by the claims, and can include other examples that occur to those persons of ordinary skill in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A sanitizing system comprising:
a dispensing unit having a fluid storage and a compressed air generator, the fluid storage storing one or more disinfecting fluids or other sanitizing agents;
an interconnect configured as an adapter that defines a conduit or passageway in an airflow path between a ground air supply preconditioned air unit and a connection port on an aircraft, wherein the dispensing unit is configured to dispense the one or more disinfecting fluids or other sanitizing agents into the airflow path via the interconnect, wherein the interconnect has a cylindrical shape with an inlet side of the interconnect being removably mateable with an outlet of the ground air supply preconditioned air unit via a first set of coupling members associated with the preconditioned air unit, wherein an outlet side of the interconnect is positioned directly opposite to the inlet side of the interconnect, wherein the outlet side of the interconnect is removably mateable with the connection port on the aircraft via a second set of coupling members associated with the interconnect, and wherein a dispensing end of the dispensing unit is located within the interconnect; and a nozzle within the interconnect configured to dispense the one or more disinfecting fluids or other sanitizing agents using compressed air generated by the compressed air generator, wherein the dispensing unit comprises a controller that controls activation and deactivation of the dispensing unit including an amount and time period during which the one or more disinfecting fluids or the other sanitizing agents are dispensed based on a size of the aircraft, wherein the controller is configured to control the activation and the deactivation of the dispensing unit based on sensor feedback that indicates a level of sanitation to be used to adjust one or more settings for dispensing the disinfecting fluid or the other sanitizing agents, wherein the compressed air generator comprises a blower that is positioned below and removably coupled to the fluid storage that comprises a mixing chamber and wherein the blower is configured to drive air to and through the mixing chamber, wherein the nozzle is oriented in the mixing chamber to introduce the one or more disinfecting fluids or other sanitizing agents in a direction of airflow provided by the blower.

2. The sanitizing system of claim 1, wherein the nozzle is positioned within the airflow path into the aircraft.

3. The sanitizing system of claim 1, wherein the connection port on the aircraft is an inlet port to an environmental control system (ECS) of the aircraft.

4. The sanitizing system of claim 1, wherein the interconnect is configured to couple inline between the ground air supply preconditioned air unit and the connection port.

5. The sanitizing system of claim 1, wherein the dispensing unit is housed within a ground cart.

6. The sanitizing system of claim 1, wherein the nozzle forms part of an electrostatic spray gun.

7. The sanitizing system of claim 1, wherein the dispensing unit comprises a first nozzle configured to dispense a first type of the one or more disinfecting fluids or other sanitizing agents using, wherein the first nozzle is exchangeable with a second nozzle configured to dispense a different second type of the one or more disinfecting fluids or other sanitizing agents using.

8. The sanitizing system of claim 1, wherein the controller is configured to initiate dispersal of the one or more disinfecting fluids or the other sanitizing agents in response to automatic detection of no passengers being present in a cabin of the aircraft via a sensor.

9. A sanitizing system comprising:

a dispensing unit having a fluid storage and a compressed air generator, the fluid storage storing one or more disinfecting fluids or other sanitizing agents;

a ground air supply preconditioned air unit (PCA);

an interconnect configured as an adapter that defines a conduit or passageway in an airflow path between the ground air supply preconditioned air unit and a connection port on an aircraft, wherein the dispensing unit is configured to dispense the one or more disinfecting fluids or other sanitizing agents into the airflow path via the interconnect, wherein the interconnect has a cylindrical shape with an inlet side of the interconnect being removably mateable with an outlet of the ground air supply preconditioned air unit via a first set of coupling members associated with the preconditioned air unit, wherein an outlet side of the interconnect is positioned directly opposite to the inlet side of the interconnect, wherein the outlet side of the interconnect is removably mateable with the connection port on the aircraft via a second set of coupling members associated with the interconnect, and wherein a dispensing end of the dispensing unit is located within the interconnect; and a nozzle within the interconnect configured to dispense the one or more disinfecting fluids or other sanitizing agents using compressed air generated by the compressed air generator, wherein the dispensing unit comprises a controller that controls activation and deactivation of the dispensing unit including an amount and time period during which the one or more disinfecting fluids or the other sanitizing agents are dispensed based on a size of the aircraft, wherein the controller is configured to control the activation and the deactivation of the dispensing unit based on sensor feedback that indicates a level of sanitation to be used to adjust one or more settings for dispensing the disinfecting fluid or the other sanitizing agents, wherein the compressed air generator comprises a blower that is positioned below and removably coupled to the fluid storage that comprises a mixing chamber and wherein the blower is configured to drive air to and through the mixing chamber, wherein the nozzle is oriented in the mixing chamber to introduce the one or more disinfecting fluids or other sanitizing agents in a direction of airflow provided by the blower.

10. The sanitizing system of claim 9, wherein the nozzle is positioned within the airflow path into the aircraft.

11. The sanitizing system of claim 9, wherein the connection port on the aircraft is an inlet port to an environmental control system (ECS) of the aircraft.

12. The sanitizing system of claim 9, wherein the interconnect is configured to couple inline between the ground air supply preconditioned air unit and the connection port.

13. The sanitizing system of claim 9, wherein the dispensing unit is housed within a ground cart.

14. The sanitizing system of claim 9, wherein the nozzle forms part of an electrostatic spray gun.

15. The sanitizing system of claim 9, wherein the dispensing unit comprises a first nozzle configured to dispense a first type of the one or more disinfecting fluids or other sanitizing agents using, wherein the first nozzle is exchangeable with a second nozzle configured to dispense a different second type of the one or more disinfecting fluids or other sanitizing agents using.

16. The sanitizing system of claim 9, wherein the controller is configured to initiate dispersal of the one or more disinfecting fluids or the other sanitizing agents in response to automatic detection of no passengers being present in a cabin of the aircraft via a sensor.

17. A sanitizing system comprising:

a dispensing unit having a fluid storage and a compressed air generator, the fluid storage storing one or more disinfecting fluids or other sanitizing agents;

an interconnect configured as an adapter that defines a conduit or passageway in an airflow path between a ground air supply preconditioned air unit and a connection port on an aircraft, wherein the dispensing unit is configured to dispense the one or more disinfecting fluids or other sanitizing agents into the airflow path via the interconnect, wherein the interconnect comprises an inlet side of the interconnect being removably mateable with an outlet of the ground air supply preconditioned air unit via a first set of coupling members associated with the preconditioned air unit, wherein an outlet side of the interconnect is positioned directly opposite to the inlet side of the interconnect, wherein the outlet side of the interconnect is removably mateable with the connection port on the aircraft via a second set of coupling members associated with the interconnect, and wherein a dispensing end of the dispensing unit is located within the interconnect; and a nozzle within the interconnect configured to dispense the one or more disinfecting fluids or other sanitizing agents using compressed air generated by the compressed air generator, wherein the dispensing unit comprises a controller that controls activation and deactivation of the dispensing unit including an amount and time period during which the one or more disinfecting fluids or the other sanitizing agents are dispensed based on a size of the aircraft, wherein the compressed air generator comprises a blower that is positioned below and removably coupled to the fluid storage that comprises a mixing chamber and wherein the blower is configured to drive air to and through the mixing chamber, wherein the nozzle is oriented in the mixing chamber to introduce the one or more disinfecting fluids or other sanitizing agents in a direction of airflow provided by the blower.

18. The sanitizing system of claim 17, wherein the controller is configured to control the activation and the deactivation of the dispensing unit based on sensor feedback that indicates a level of sanitation to be used to adjust one or more settings for dispensing the disinfecting fluid or the other sanitizing agents.

19. The sanitizing system of claim 17, wherein the controller is configured to initiate dispersal of the one or more disinfecting fluids or the other sanitizing agents in response to automatic detection of no passengers being present in a cabin of the aircraft via a sensor.

20. The sanitizing system of claim 17, wherein the dispensing unit comprises a first nozzle configured to dispense a first type of the one or more disinfecting fluids or other sanitizing agents using, wherein the first nozzle is exchangeable with a second nozzle configured to dispense a different second type of the one or more disinfecting fluids or other sanitizing agents using.

* * * * *